US008691520B2

(12) United States Patent
Andreescu et al.

(10) Patent No.: US 8,691,520 B2
(45) Date of Patent: Apr. 8, 2014

(54) REAGENTLESS CERIA-BASED COLORIMETRIC SENSOR

(75) Inventors: Emanuela Silvana Andreescu, Potsdam, NY (US); Maryna Ornatska, Potsdam, NY (US); Cristina R. Ispas, Brea, CA (US); Daniel Andreescu, Potsdam, NY (US)

(73) Assignee: Clarkson University, Potsdam, NY (US)

( * ) Notice: Subject to any disclaimer, the term of this patent is extended or adjusted under 35 U.S.C. 154(b) by 120 days.

(21) Appl. No.: 13/156,755

(22) Filed: Jun. 9, 2011

(65) Prior Publication Data

US 2012/0315659 A1 Dec. 13, 2012

(51) Int. Cl.
*C12Q 1/48* (2006.01)

(52) U.S. Cl.
USPC .............................................. 435/25; 435/15

(58) Field of Classification Search
None
See application file for complete search history.

(56) References Cited

U.S. PATENT DOCUMENTS

| | | | |
|---|---|---|---|
| 3,721,607 | A | 3/1973 | Gruber et al. |
| 7,504,356 | B1 | 3/2009 | Self et al. |
| 2009/0071848 | A1 | 3/2009 | Seal et al. |

FOREIGN PATENT DOCUMENTS

| | | |
|---|---|---|
| WO | 2006130473 | 7/2006 |

OTHER PUBLICATIONS

Barnard et al., Infection and Immunity, vol. 67, No. 12, pp. 6558-6564, Dec. 1999.*

Babko, A. K. and Volkova, A. I., 1954, "The Colored Peroxide Complex of Cerium", Ukrains'kii Khemichnii Zhurna 20: pp. 211-215.

Beach, E. F. and Turner, J. J., 1958, "An Enzymatic Method for Glucose Determination in Body Fluids", Clinical Chemistry 4(6); pp. 462-475.

Dungchai, W., Chailapakul, O., et al., 2010, "Use of Multiple Colorimetric Indicators for Paper-based Microfluidic Devices", Analytica Chimica Acta, 674(2): pp. 227-233.

Ispas, C., Njagi, J., et al., 2008, "Electrochemical Studies of Ceria as Electrode Material for Sensing and Biosensing Applications," Journal of the Electrochemical Society 155(8): pp. F169-F176.

Martinez, A., Phillips, S., et al., 2007, "Patterned Paper as a Platform for Inexpensive, Low-Volume, Portable Bioassays", Angewandte Chemie International Edition 46(8): pp. 1318-1320.

Mehta, A., Patil, S., et al., 2007, "A Novel Multivalent Nanomaterial Based Hydrogen Peroxide Sensor", Sensors and Actuators a-Physical 134(1): pp. 146-151.

Trinder, P., 1969, "Determination of Blood Glucose Using 4-Amino Phenazone as Oxygen Acceptor", Journal of Clinical Pathology 22(2): p. 246.

Yu, P., Hayes, S. A., et al., 2006, "The Phase Stability of Cerium Species in Aqueous Systems—II. The Ce(III/IV)-H2O-H2O2/O-2 Systems. Equilibrium Considerations and Pourbaix Diagram Calculations", Journal of the Electrochemical Society 153(1): pp. C74-C79.

Patil, S. D., Fundamental Aspects of Regenerative Cerium Oxide Nanoparticles and Their Applications in Nanobiotechnology (Ph.D. Thesis), University of Central Florida, Orlando, 2006, pp. 1-126.

Ornatska, M. et al., Paper Bioassay Based on Ceria Nanopoarticles as Colorimetric Probes, Analytical Chemistry, Apr. 28, 2011, vol. 83, pp. 4273-4280.

International Search Report Form PCT/ISA/220, International Application No. PCT/2012/041608, pp. 1-12, Dated Dec. 24, 2012.

* cited by examiner

*Primary Examiner* — Richard Hutson

(74) *Attorney, Agent, or Firm* — George R. McGuire; Blaine T. Bettinger; Bond Schoeneck & King, PLLC

(57) ABSTRACT

A colorimetric reagent in the form of nanoparticles, composite nanoparticles, and nanoparticle coatings, including methods of use, methods of preparation, deposition, and assembly of related devices and specific applications. The colorimetric reagent comprises cerium oxide nanoparticles which are used in solution or immobilized on a solid support, either alone or in conjunction with oxidase enzymes, to form an active colorimetric component that reacts with an analyte to form a colored complex. The rate of color change and the intensity of the color are proportional to the amount of analyte present in the sample. Also described is the use of ceria and doped ceria nanoparticles as an oxygen storage/delivery vehicle for oxidase enzymes and applications in biocatalytic processes in anaerobic conditions of interest in biomedicine and bioanalysis. Further described are a variety of related applications of the disclosed technology including clinical diagnosis, in vivo implantable devices, food safety, and fermentation control.

19 Claims, 7 Drawing Sheets

REAGENTLESS CERIA-BASED COLORIMETRIC SENSOR

BACKGROUND OF THE INVENTION

1. Field of the Invention

The present invention relates to components, methods, and analytical devices for fast point of care or field colorimetric analysis. More specifically, the invention relates to the use of nanoparticles as active color agents to fabricate colorimetric assays for the detection of substances and to their practical applications in a variety of fields including clinical diagnosis, environmental and food.

2. Description of the Related Art

The invention consists of a colorimetric assay (including a method, test device, test strip, detection kit, biosensor) for the visual analysis of chemical substances in various samples. The method incorporates a new concept based on a novel colorimetric component. The colorimetric component refers to nanoparticles of cerium oxide, or ceria, which change the color in response to the presence of a particular analyte, and of cerium oxide nanoparticles in close contact with specific oxidase enzymes, in response to a substrate or product of the enzymatic reaction. The nanoparticles can be used in solution, or attached to a solid support to construct a device. The device is fabricated by immobilizing cerium oxide nanoparticles with and without enzymes onto a solid support. Examples of suitable solid supports include but are not limited to paper, ceramics, membrane, packaging materials, polymeric support, cotton swab, patch, test tube, wipe, gas or fluid collection device, sponge, and lens. The device can be used to determine quantitatively the presence and the relative concentration of chemicals including, but not limited to, hydrogen peroxide, reactive oxygen species and free radicals, ethanol, glucose, cholesterol, billirubin, glutamate, lactate, and various antioxidants.

Hydrogen peroxide is a key component in many chemical, biological, pharmaceutical, clinical, environmental and food processes. The availability of a reliable, efficient and economic method for its detection is of great practical importance. For example, the use of hydrogen peroxide has become a popular method of water treatment because peroxide is effective in elimination of bacteria and moulds. Cheap and effective monitoring methods of hydrogen peroxide in pools, hot tubs and drinking water are needed. Monitoring peroxide concentrations is also important in hospitals where hydrogen peroxide is used as a sterilizing and cleaning solution. Because hydrogen peroxide is prone to decomposition, losing its antibacterial potency overtime, periodic confirmation of the concentration of these solutions is necessary. At the same time, hydrogen peroxide is an indicator of inflammation and it is known that wound-induced extracellular H2O2 may reach concentrations of 0.5-50 mM near the wound area. Fast detection kits of hydrogen peroxide could also find potential uses for screening of hydrogen peroxide-generating bacteria, (e.g. lactic acid bacteria), present in healthy human micro flora and in food industry (e.g. milk products, sausage production). In addition, hydrogen peroxide is the by-product of many enzymatic reactions of oxidase enzymes (e.g. glucose oxidase, lactate oxidase, glutamate oxidase, cholesterol oxidase, alcohol oxidase, etc) and its detection represents the basis of numerous enzyme biosensors e.g. for quantitative determination of glucose, lactate, glutamate, cholesterol, ethanol, etc). Quantitative analysis of hydrogen peroxide as well as oxidase enzyme substrates listed above has been accomplished using electrochemical methods based on direct reduction or oxidation of H2O2 at the surface of a chemically or enzymatically modified working electrode. Such systems are used in conjunction with reference/counter electrodes and a potentiostat.

Several colorimetric test strip devices for these substances have been reported. These devices use colorimetric reagents (e.g. soluble dyes), fluorescent compounds, redox reagents and enzymes, to quantitatively determine specific substances in a sample. In previous reports, an oxidase enzyme (e.g. glucose oxidase, cholesterol oxidase, alcohol oxidase, etc), in solution or immobilized onto a solid surface constituting the sensing area, is used to catalytically transform the enzyme substrate (glucose, cholesterol, ethanol, etc) to hydrogen peroxide. The enzymatically generated hydrogen peroxide is subsequently measured using chromogenic substances and spectrophotometric analysis. The response of the sensor is based on a color change of a dye, added in solution, in response to a chemical and/or enzymatic reaction. The intensity of the color is typically compared to that of several standard color charts obtained with known concentrations of analyte. In many cases these test strips involve the use of multiple compartments and separate reagents (chromogens for the color change, enzymes, co-substrates, etc) that need to be added in order to initiate the desired colored reaction. In most cases, ABTS (2, 2'-azino-di(3-ethylbenzthiazoline-6-sulfonate) is used as a chromogenic compound for the detection of hydrogen peroxide. In previously developed paper based enzymatic assays, the soluble dye (e.g. KI) migrates to the sensing spot by capillary action. In the new colorimetric assay described here, redox active ceria nanoparticles are used as a chromogenic indicator for H2O2, eliminating the need for both the organic dye and the peroxidase enzyme.

Traditionally, cerium oxide or ceria, or $CeO_2$, has been used in catalytic applications like automotive combustion engines, industrial chemical synthesis and solid oxide fuel cells. Recently, ceria has found new applications in biomedicine due to its interesting catalytic and radical scavenging properties, and its low toxicity. The hydroxylated cerium (IV) ions form a reddish orange complex with hydrogen peroxide. This interesting property first discovered by de Boisbaudran was used as the most sensitive test for cerium ions but it has not been utilized as a test for the analysis of other compounds. Later studies have shown that this reaction has two stages: (1) oxidation of Ce(III) to Ce (IV), and (2) complexation of Ce(IV) ion with two molecules of hydrogen peroxide. Ceria nanoparticles are comprised of cerium oxides in mixed valence states both as Ce(III) and Ce(IV) with lower size particles having higher percentage of Ce(III) valence states. This invention is the first to: (1) use ceria nanoparticles as chromogenic indicators in an enzyme assay; (2) immobilize ceria onto a solid support such as paper; and (3) integrate this concept to construct a paper bioassay for the detection of glucose for point-of-care ("POC") diagnostics.

An electrochemical hydrogen peroxide sensing system is disclosed in Patent No. US 2009/0071848 entitled: "Cerium oxide nanoparticle regenerative radical sensor" by Seal et al. (Seal, Cho et al. 2006). Electrochemical detection of hydrogen peroxide is also described in two research papers (Ispas, Njagi et al. 2008) (Mehta, Patil et al. 2007). In these systems, ceria was used as electrode coating and the signal was obtained by electrochemical means. Such system can be used only in combination with an electrochemical transducer and involves the use of reference/counter electrodes and specialized electrochemical instrumentation (e.g. potentiostat). The sensor is limited to the detection of hydrogen peroxide and superoxide radicals. It is also used in conjunction with platinum, which is an expensive catalyst for hydrogen peroxide by itself. In addition, that sensor might be prone to interferences from other electrochemically active species which can be oxidized or reduced at the applied potential such as hydrogen peroxide.

The relevant art is described in further detail in the following references, all of which are hereby incorporated by reference: Babko, A. K. and A. I. Volkova (1954), "The colored peroxide complex of cerium," *Ukrains'kii Khemichnii Zhurna* 20: 211-215; Beach, E. F. and J. J. Turner (1958), "An enzymatic method for glucose determination in body fluid," *Clinical Chemistry* 4(6); 462-475; Dungchai, W., O. Chailapakul, et al. (2010), "Use of multiple colorimetric indicators for paper-based microfluidic devices." *Analytica Chimica Acta* 674(2): 227-233; Ispas, C., J. Njagi, et al. (2008), "Electrochemical studies of ceria as electrode material for sensing and biosensing applications," *Journal of the Electrochemical Society* 155(8): F169-F176; Martinez, A., S. Phillips, et al. (2007), "Patterned Paper as a Platform for Inexpensive, Low-Volume, Portable Bioassays," *Angewandte Chemie International Edition* 46(8): 1318-1320; Mehta, A., S. Patil, et al. (2007), "A novel multivalent nanomaterial based hydrogen peroxide sensor," *Sensors and Actuators a-Physical* 134(1): 146-151; Seal, S., H. Cho, et al. (2006), "Cerium oxide nanoparticle regenerative free radical sensor," USA, University of Central Florida, USA. WO 2006130473, US 20090071848: 19 pp; Trinder, P. (1969), "Determination of blood glucose using 4-amino phenazone as oxygen acceptor," *Journal of Clinical Pathology* 22(2): 246; Wolfgang, G., U. B. Hans, et al. (1973), "Reagent composition and process for the determination of glucose," Germany, Boehringer, Mannheim GmbH, U.S. Pat. No. 3,721,607; and Yu, P., S. A. Hayes, et al. (2006), "The phase stability of cerium species in aqueous systems—II. The Ce(III/IV)-H2O-H2O2/O-2 systems. Equilibrium considerations and pourbaix diagram calculations." *Journal of the Electrochemical Society* 153(1): C74-C79.

BRIEF SUMMARY OF THE INVENTION

It is therefore a principal object and advantage of the present invention to use ceria as a chromogenic indicator in an enzyme assay.

It is another object and advantage of the present invention to provide a system that immobilizes ceria onto a solid support.

It is yet another object and advantage of the present invention to construct a ceria-based bioassay for the detection of glucose for point-of-care ("POC") diagnostics.

Other objects and advantages of the present invention will in part be obvious, and in part appear hereinafter.

In accordance with the foregoing objects and advantages, the present invention takes advantage of the color change of ceria nanoparticles in the presence of hydrogen peroxide and antioxidants such as ascorbic acid, thus making possible their detection; the disclosed system is based on colorimetric detection. The concentration can be distinguished with the naked eye without special transduction systems.

The invention also demonstrates the use of ceria nanoparticles in conjunction with oxidative enzymes, thus providing selectivity through biocatalysis. The invention discloses a new capacity of ceria nanoparticles when used in conjunction with oxidase enzymes: the oxygen storage capacity for biocatalysis. This property provides possibilities for operation of oxidase enzymes in anaerobic conditions, thus expanding the range of analytes that can be detected and the application field of this new device. The disclosed device can thus be adapted for detecting a variety of analytes and be used in numerous applications; the system can detect virtually any oxidase enzyme substrate in both aerobic and anaerobic conditions.

Taking advantage of the property of cerium oxide nanoparticles as described above, disclosed is a new colorimetric test strip design in which ceria nanoparticles are used as color indicator reagent instead of a soluble dye. In another embodiment of the invention, the new colorimetric component (based on ceria nanoparticles) is used in solution. In yet another embodiment of this invention, all the necessary components are conveniently attached to a solid support to form the sensing surface and construct a new type of ceria based device, test strip, biosensor. The new device described in the present invention is inexpensive, easy to fabricate and reagentless: the only needed step for analysis is sample addition to bring the analyte in contact with the sensing surface. In a preferred embodiment, the system comprises a single compartment of active sensing material consisting of a layer of immobilized cerium oxide nanoparticles, or cerium oxide nanoparticles co-immobilized with oxidase enzymes. The sensing materials can be deposited onto a solid support, such as: paper, ceramics, packaging materials, wipes, glass, plastic, cotton swabs, patches, bag, lenses, gas or fluid collection device or other porous substrates. The same principle can also be used by placing all components of the assay in solution, in a test tube. This new device would be used primarily for analysis of liquid samples but the application is not restricted to liquids; analysis of gaseous samples such as breath ethanol is also possible. The device is regenerable and can be used for analysis of multiple samples. In addition, the device can function in conditions of oxygen depletion such as anaerobic fermentation environments, in vivo implantable conditions, analysis in deep oceans, space, etc.

There are many embodiments of the invention. In some embodiments the invention include a colorimetric ceria component as a color reagent that can be used in solution for direct colorimetric detection of: (1) hydrogen peroxide, (2) antioxidants (such as ascorbic acid, gallic acid, vanillic acid, caffeic acid, trolox. resveratrol, quercetin, etc) and (3) for detection of hydrogen peroxide formed by specific enzymes. It also includes the use of colorimetric ceria in immobilized state, attached to solid supports alone or in conjunction with enzymes. In another embodiment, the invention includes the operation of the described ceria based systems incorporating oxidase enzymes, both in solution and immobilized, either in aerobic or anaerobic conditions. In another embodiment, this invention includes descriptions of the fabrication of ceria-based colorimetric test devices and ceria based biosensors. Examples of specific applications of the new disclosed devices for semi-quantitative detection of analytes in various samples including clinical: whole blood, urine, saliva, human breath, etc, environmental and food samples, including applications in food packaging; both liquid and gaseous samples can be determined. Applications to in vivo implantable devices are also included.

Therefore, in accordance with the foregoing objects and advantages, the present invention provides a method for the colorimetric detection of hydrogen peroxide in a sample comprising the steps of: (i) providing a colorimetric reagent comprising a plurality of ceria nanoparticles; (ii) contacting the colorimetric reagent with the sample to form a mixture; and (iii) detecting an optical property of the mixture, where a change in the optical property of the mixture is associated with the presence of hydrogen peroxide in the mixture.

According to a second aspect of the present invention is provided a method for the colorimetric detection of an analyte in a sample comprising the steps of: (i) providing a colorimetric reagent comprising a plurality of ceria nanoparticles and a plurality of analyte-specific oxidase enzyme molecules; (ii) contacting the colorimetric reagent with a sample to form a mixture, where at least some of the plurality of oxidase enzyme molecules react with the analyte to form hydrogen peroxide; and (iii) detecting an optical property of the mixture, where a change in the optical property of the mixture is associated with the presence of hydrogen peroxide or antioxidants in the mixture. In a preferred embodiment, the change in the optical property is proportional to the concentration of the analyte in the sample. The colorimetric reagent can be in solution or immobilized to a support. In a preferred embodiment, the colorimetric reagent does not comprise a dye. In yet another embodiment of the present invention, the step of contacting the colorimetric reagent with a sample to form a mixture comprises contacting the colorimetric reagent with a sample under anaerobic conditions According to a third aspect of the present invention is provided a method for the colorimetric detection of an analyte in a sample comprising the steps of: (i) providing a colorimetric reagent comprising a plurality of ceria nanoparticles and a plurality of analyte-specific oxidase enzyme molecules; (ii) contacting the colorimetric reagent with a sample to form a mixture, where at least some of the plurality of oxidase enzyme molecules react with the analyte to form hydrogen peroxide; (iii) detecting an optical property of the mixture, where a change in the optical property of the mixture is associated with the presence of hydrogen peroxide in the mixture; and (iv) comparing the optical property of the mixture to a pre-determined value. In a preferred embodiment, the plurality of ceria nanoparticles comprise cerium oxides in at least two different valence states, and have a diameter ranging from about 2 nm to about 20 nm. Further, in yet another embodiment of the present invention the ceria nanoparticles are doped with a metal selected from the group consisting of platinum, gold, palladium, manganese, osmium, gadolinium, samarium, niobium, dysprosium, erbium, germanium, holmium, indium, iridium, molybdenum, neodymium, rhodium, tantalum, tungsten, yttrium, zirconium, ytterbium, thulium, terbium, praseodymium, and combinations thereof.

According to a fourth aspect of the present invention, the analyte-specific oxidase enzyme molecule is selected from the group including, but not limited to, alcohol oxidase, glucose oxidase, cholesterol oxidase, glutamate oxidase, galactose oxidase, lactate oxidase, and combinations thereof. In a preferred embodiment, the analyte is selected from the group including, but not limited to, ethanol, glucose, cholesterol, glutamate, galactose, billirubin, lactate, and combinations thereof.

According to a fifth aspect of the present invention is provided a method for the colorimetric detection of an analyte in a sample comprising the steps of: (i) providing a colorimetric reagent comprising a plurality of ceria nanoparticles and a plurality of analyte-specific oxidase enzyme molecules; (ii) contacting the colorimetric reagent with a sample to form a mixture, where at least some of the plurality of oxidase enzyme molecules react with the analyte to form hydrogen peroxide; (iii) detecting an optical property of the mixture, where a change in the optical property of the mixture is associated with the presence of hydrogen peroxide in the mixture; and (iv) reusing the colorimetric reagent. In a preferred embodiment, the colorimetric reagent can be used after a certain time period, and/or after a period of heating.

According to a sixth aspect of the present invention is provided a system for the colorimetric determination of an analyte in a sample, the system comprising: (i) a sample; and (ii) a colorimetric reagent comprising a plurality of ceria nanoparticles and a plurality of analyte-specific oxidase enzyme molecules. In a preferred embodiment, the colorimetric reagent is immobilized on a support such as cellulose paper, cotton, silk and/or synthetic materials such as porous glass, cross-linked polymers and co-polymers, contact lenses, or plastic/glass test tubes. In yet another embodiment of the present invention, the colorimetric reagent further comprises a stabilizing agent and/or a linking agent.

According to a seventh aspect of the present invention is provided a method for the colorimetric detection of an antioxidant in a sample comprising a predetermined amount of analyte, the method comprising the steps of: (i) providing a colorimetric reagent comprising a plurality of ceria nanoparticles and a plurality of oxidase enzyme molecules specific to the analyte; (ii) contacting the colorimetric reagent with a sample to form a first mixture, wherein at least some of the plurality of oxidase enzyme molecules react with the analyte to form hydrogen peroxide; (iii) detecting an optical property of the first mixture; and (iv) comparing a change in the optical property of the first mixture to a change in an optical property of a second mixture under the same conditions but in the absence of said antioxidant, wherein a decrease in the change in the optical property of the first mixture compared to the change in the optical property of the second mixture is associated with the presence of said antioxidant.

According to an eighth aspect of the present invention is provided a method for the colorimetric detection of an antioxidant, the method comprising the steps of (i) providing a colorimetric reagent comprising a plurality of ceria nanoparticles; (ii) contacting the colorimetric reagent with a sample to form a mixture; and (iii) detecting an optical property of the first mixture, wherein a change in the optical property of the mixture is associated with the presence of the antioxidant.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 3:
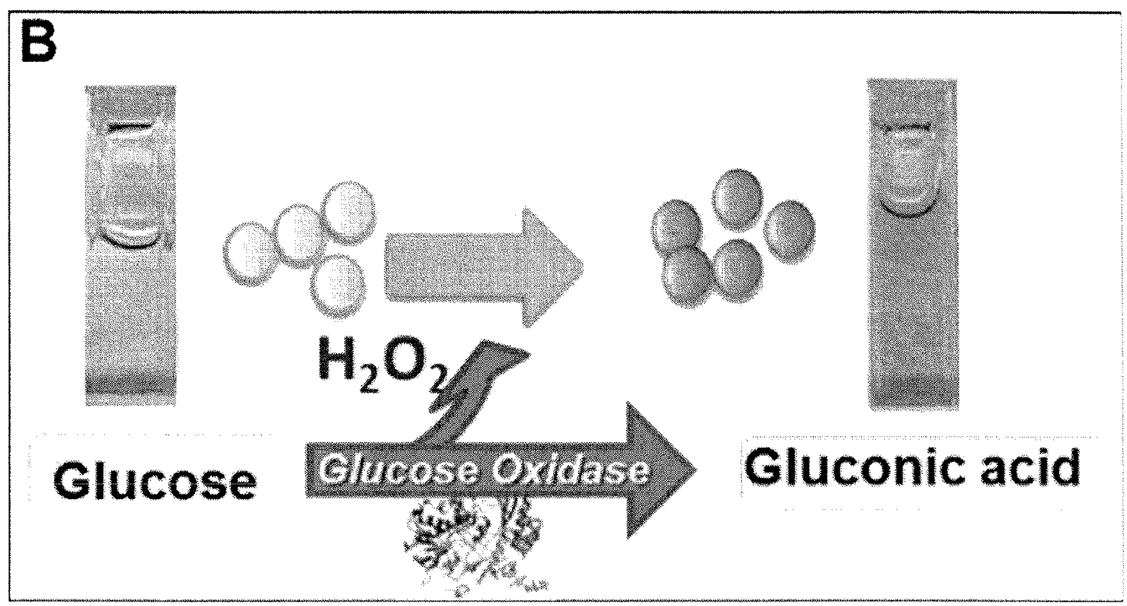

FIG. 3 is a schematic of the working principle of the ceria nanoparticle bioassay for the detection of oxidase enzyme substrates showing detection of glucose as a model example; the particles and the enzyme are co-immobilized onto a paper platform and the only step needed to perform the analysis is the addition of the analyte. The visible color change from white-yellowish to dark orange in the presence of glucose is due to the change of the oxidation state and formation of surface complexes onto the ceria nanoparticle surface, induced by the enzymatically produced hydrogen peroxide.

Figure 4A:
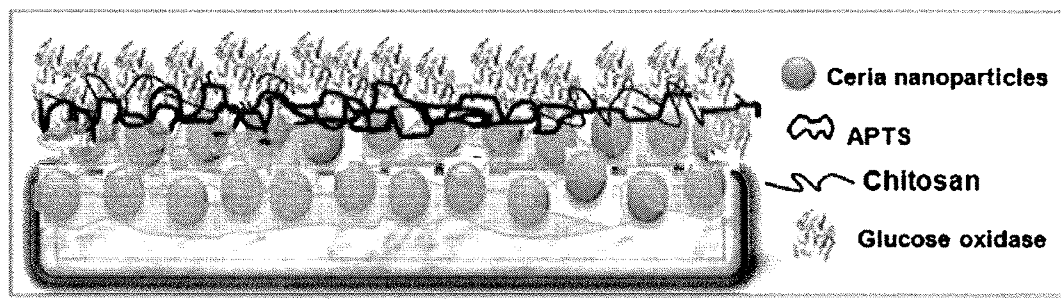

FIG. 4A is a schematic representation of immobilization of ceria nanoparticles onto paper using a silanization procedure, using a multi-layered sequence consisting of ceria nanoparticles, silica, chitosan and enzyme. Other supporting materials and procedures can also be used. The invention is not restricted to paper nor to this immobilization method; this are only provided here as an example.

Figure 4B:
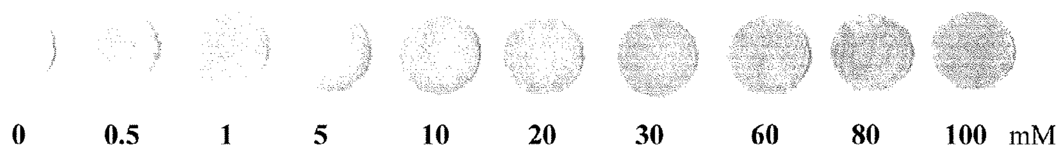

FIG. 4B is a ceria-glucose oxidase based colorimetric device on a paper substrate for semi-quantitative determination of glucose. To fabricate the assay, the enzyme is immobilized onto the paper platform, in the close proximity to the ceria nanoparticles.

Figure 5:
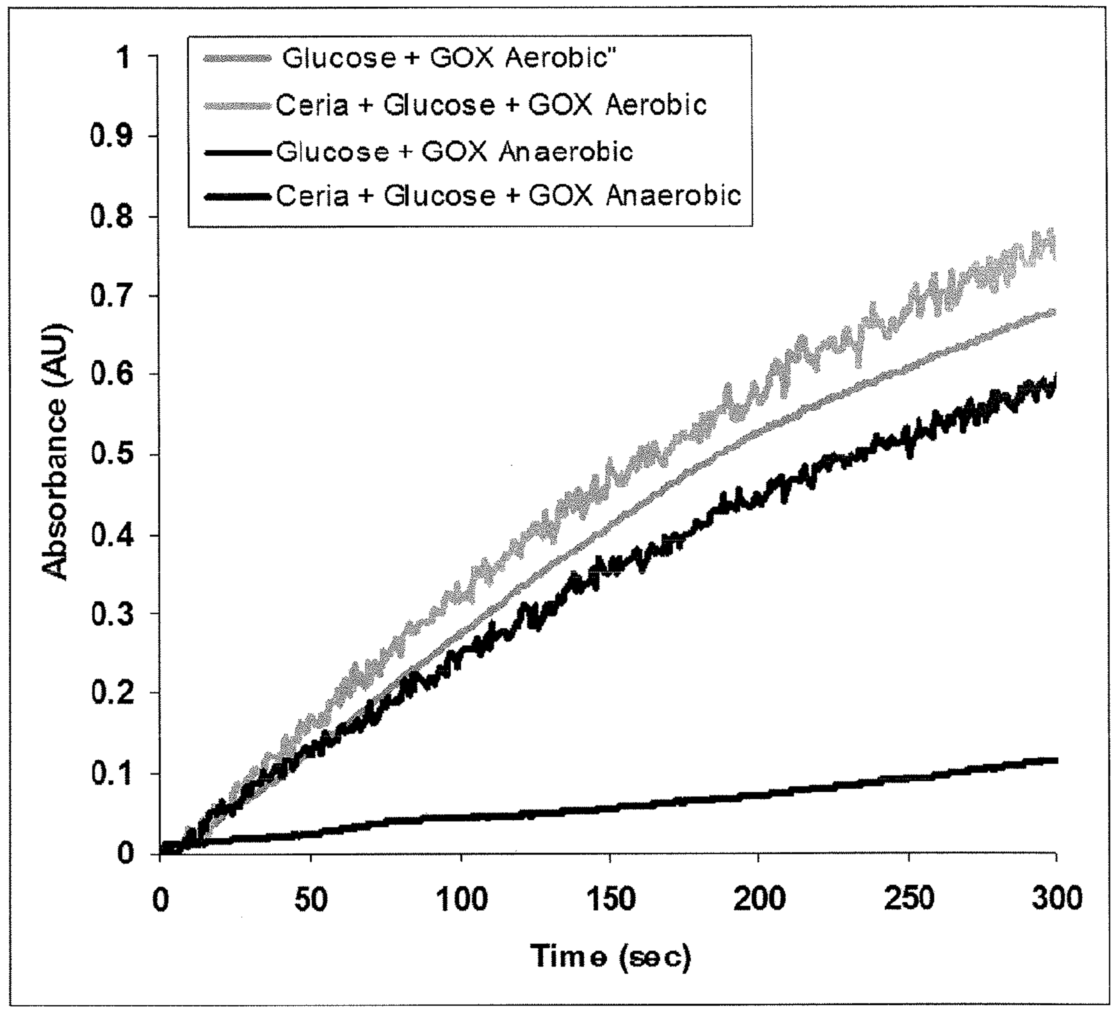

FIG. 5 is a graph of the UV-VIS spectrum of a glucose oxidase activity assay in the presence and absence of ceria in aerobic and anaerobic conditions showing that in the presence of ceria, glucose oxidase is able to catalyze the oxidation of glucose to hydrogen peroxide even in the absence of oxygen.

Figure 6:
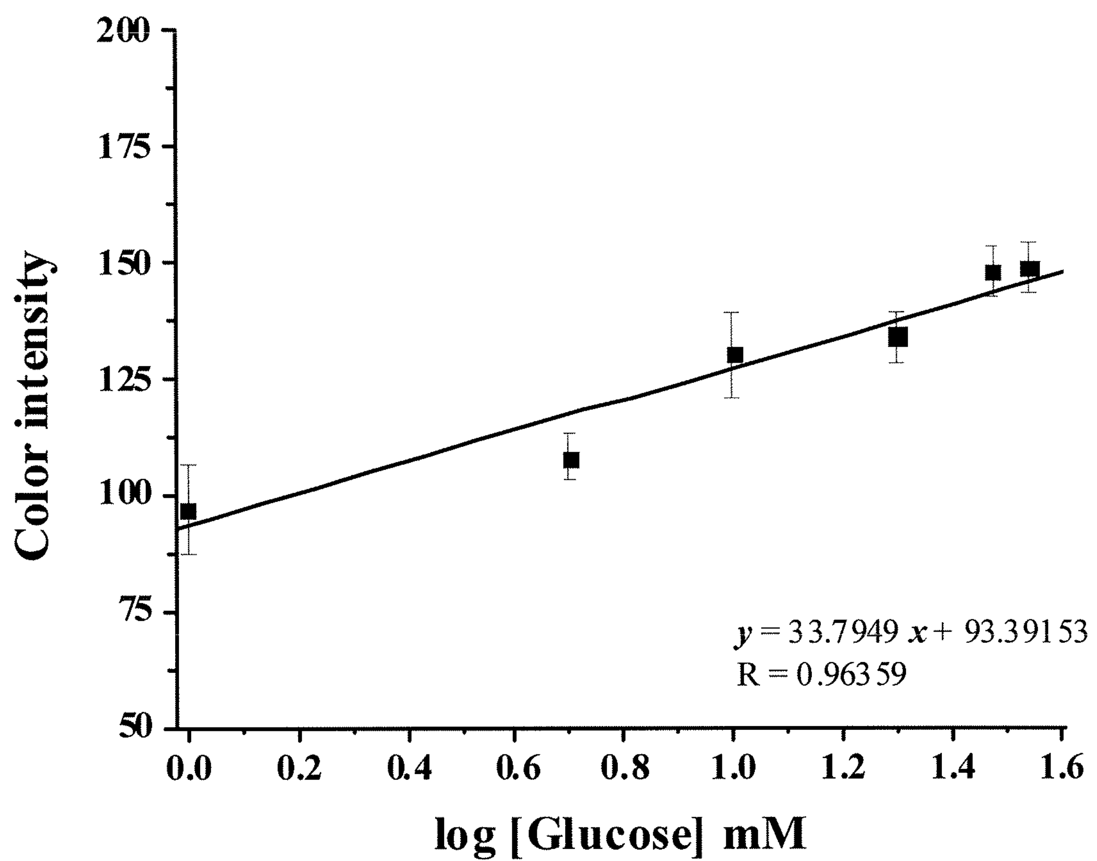

FIG. 6 is a graph of the calibration curve for glucose in human serum with the corresponding colorimetric images for each concentration tested. The intensity of the color obtained with the ceria papers in buffer in the absence of glucose was 41(+/−3.79) for n=3. In the same conditions but after addition of serum, the intensity was 74(+/−5.69), indicating that glucose is present in the serum sample. The concentration of glucose in serum determined from the calibration curve using the standard addition method was 3.71 mM.

DETAILED DESCRIPTION OF THE INVENTION

Figure 1A:
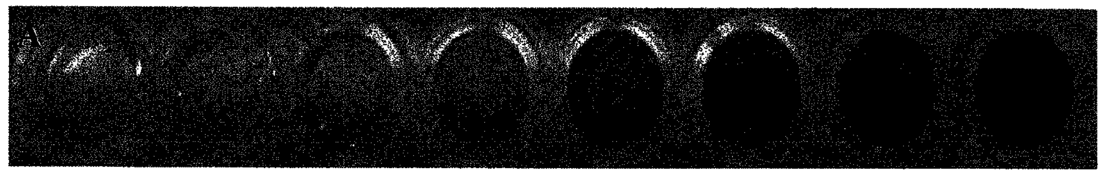
FIG. 1A depicts ceria-based colorimetric detection of hydrogen peroxide showing the color change of ceria nanoparticles in colloidal state in the presence of various concentrations of hydrogen peroxide; as the figure shows, the color change is concentration dependent.
Figure 1B:
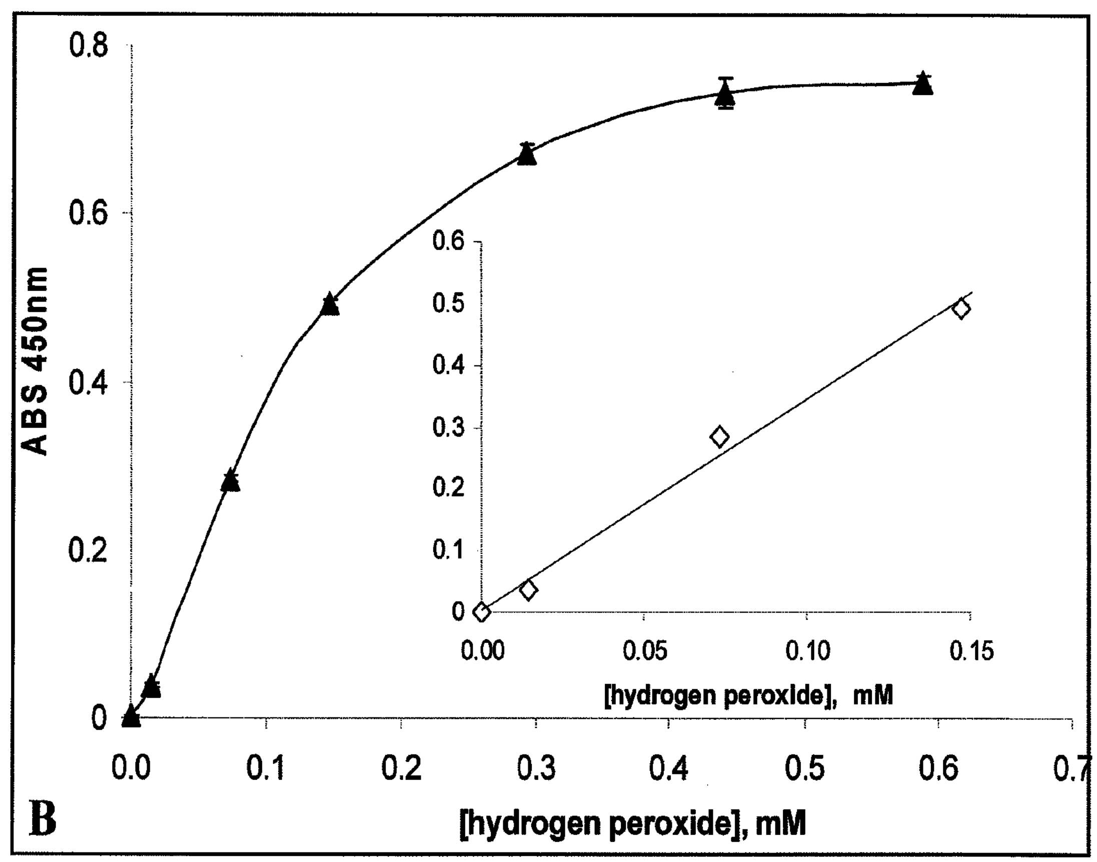
FIG. 1B is a graph of the calibration curve.
Figure 1C:
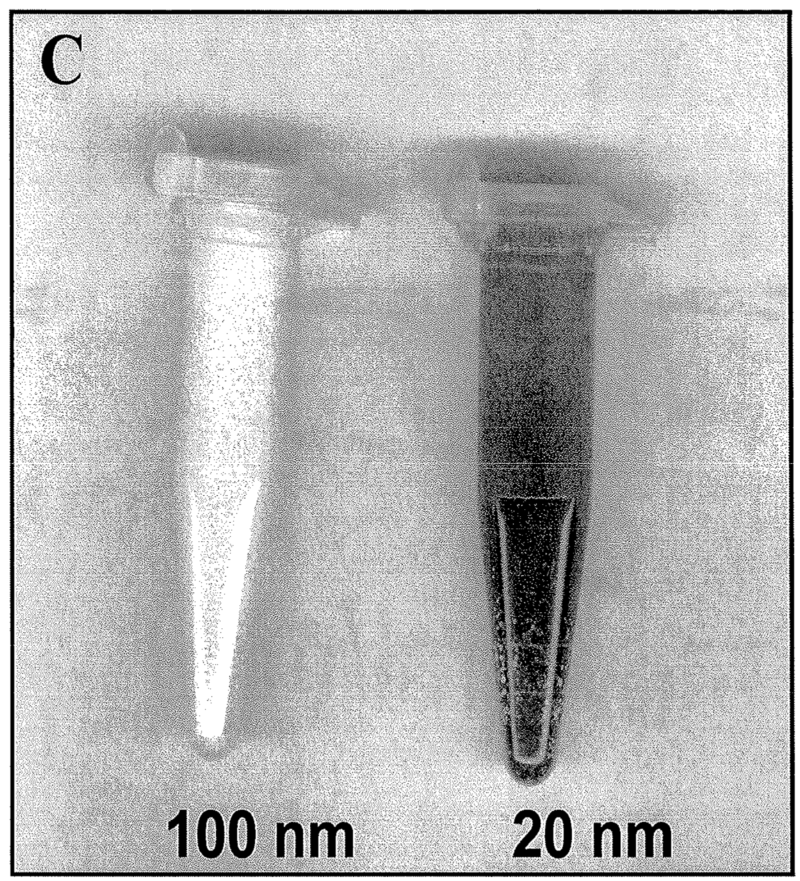
FIG. 1C depicts the effect of particle size (20 nm versus 100 nm particles).

The colorimetric test device described herein is the first reporting the use of cerium oxide nano-particles as a color indicator agent for quantitative analytical purposes. The present invention takes advantage of the color changes of ceria nanoparticles as a result of a redox process and complex formation. In particular, cerium oxide particles with a diameter ranging from 2 nm to 20 nm in colloidal solution or immobilized onto a solid support change the color almost instantaneously from white to reddish-orange in the presence of hydrogen peroxide or antioxidants. The color change is due to a change in the oxidation state of cerium from Ce(III) to Ce(IV) and formation of a cerium (IV) complex with hydrogen peroxide. This change is proportional with the concentration of hydrogen peroxide (FIGS. 1A and 1B) or antioxidants such as ascorbic acid, gallic acid, vanillic acid, caffeic acid, trolox, resveratrol, and/or quercetin, for example, in the reaction. This process is used as a basis for fabrication of a test strip comprising a colorimetric detection tool for analytes in various samples. The intensity of the color varies with the particle size (FIG. 1C): that is, a more intense color—and thus higher sensitivity and lower detection limit—is obtained with smaller size cerium oxide nanoparticles, which have a higher percentage of the Ce(III) oxidation state and a higher exposed surface area.

The device includes a sensing surface comprising of an inert adsorbent support material, containing cerium oxide nanoparticles as the colorimetric reagent, or cerium oxide nanoparticles co-immobilized with oxidase enzymes and stabilizing agents (an example is shown in FIG. 4). The supporting material may be made of one or more materials including natural materials such as cellulose paper, cotton, silk and/or synthetic materials such as porous glass, cross-linked polymers and co-polymers, contact lenses, or plastic/glass test tubes. The sensing layer containing the colorimetric nanoparticles may incorporate stabilizing agents such as surfactants and/or hydrogels. The sensing layer reacts with the analyte, resulting in a color change. The analyte may be hydrogen peroxide, free radicals, and/or antioxidants. It may also be a substrate of an oxidase enzyme such as ethanol, glucose, cholesterol, glutamate, galactose, and/or lactate, as an example. These substrates, in the presence of oxygen and its specific enzyme (alcohol oxidase, glucose oxidase, cholesterol oxidase, glutamate oxidase, galactose oxidase, lactate oxidase, etc), generates hydrogen peroxide (an example using glucose is shown in FIG. 3). The generated hydrogen peroxide will then react with the immobilized ceria changing its color in a concentration dependent manner.

In another aspect of this invention, the described test strip can be used for indirect detection of substances that inhibit the colorimetric reaction (i.e. the redox and complexation process of ceria) or the enzymatic reaction, thus preventing the formation of the color. Example include, but are not limited to, analysis of antioxidants which inactivate free radicals, or analysis of ions like $Ag^{+}$, $Hg^{2+}$, $Cu^{2+}$ which inactivate enzymes like glucose oxidase.

The device has a simple design, is inexpensive, can be mass-produced and used on site by non-skilled personnel. To manufacture the test device, the active components can be fixed (adsorbed, entrapped in polymers or sol-gel glasses, cross-linked or printed) directly onto a solid support such as paper, ceramic, glass, plastic, or other solid substrates. It can also be incorporated or attached to cotton swabs. An example of immobilization procedure using a multilayer deposition sequence is shown in FIG. 4A. A layer of the active components can be used to coat the internal surface of a transparent glass, contact lenses or plastic test tube that would, in this case form the device itself.

The test device described in this method involves applying a sample to the active surface area of the colorimetric test device based on ceria and allowing the color to develop. The presence and the amount of analyte are determined by measuring the intensity of the color or the rate of the color change and comparing it to a calibration test. This can be done either visually or by instrumental means.

Semi-quantitative visual analysis can be performed in a time period ranging from several seconds to several min, depending on the analyte. For hydrogen peroxide and antioxidants, the color develops immediately after bringing the sample in contact with the sensor (dipping, placing a drop onto the active surface, blowing gas containing the analyte, etc). For the enzymatic detection the response time is slightly higher (typically, up to several minutes). The time necessary for the development of the color can vary with the different additives, stabilizing agents and solid support used, and with, the nanoparticles size and available surface. The color is stable for several hours or days (depending on the analyte) in ambient conditions. It can be reversed when left at room temperature for several hours or within several minutes by slight heating, after the adsorbed hydrogen peroxide is decomposed. The assay can be reused for multiple cycles (at least ten times without losing analytical performance) for the detection of analytes. The measurement of color change can be made visually and comparing it with control test strips of known concentrations. More precise quantification can be performed with specialized instruments for spectrophotometric analysis. For example, the ceria-based colorimetric component defined herein can be used for photometric detection of glucose in solution mixed with glucose oxidase and measured at 450 nm vs calibration plot. The intensity of the color can also be evaluated with specialized imaging software like the ImageJ software.

In addition to the size of the ceria nanoparticles, other variabilities in the particles can result in variable outcomes. For example, ceria nanoparticles from different manufacturers and/or suppliers can have variable properties other than size, including but not limited to properties resulting from surface characteristics or the procedure and/or compounds and additives used to create the nanoparticles. Variabilities in the nanoparticles other than size may also affect the intensity, rate, or other characteristic of the color change in the presence of hydrogen peroxide. One of ordinary skill in the art would recognize that variations in the characteristics of the ceria nanoparticles will likely have some effect on the properties of the interactions and chemical reactions described herein.

Figure 2A:
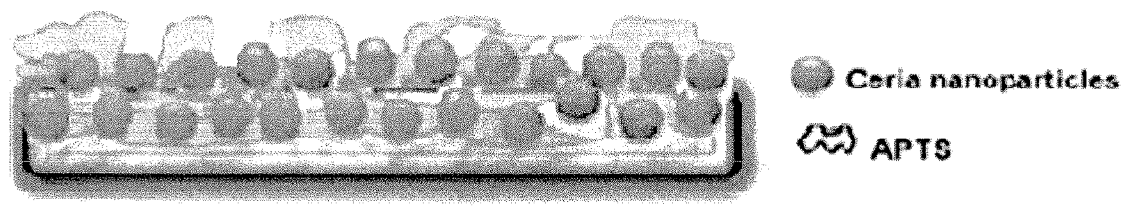
FIG. 2A is a schematic representation of ceria based colorimetric device on a paper substrate for semi-quantitative analysis of hydrogen peroxide.
Figure 2B:
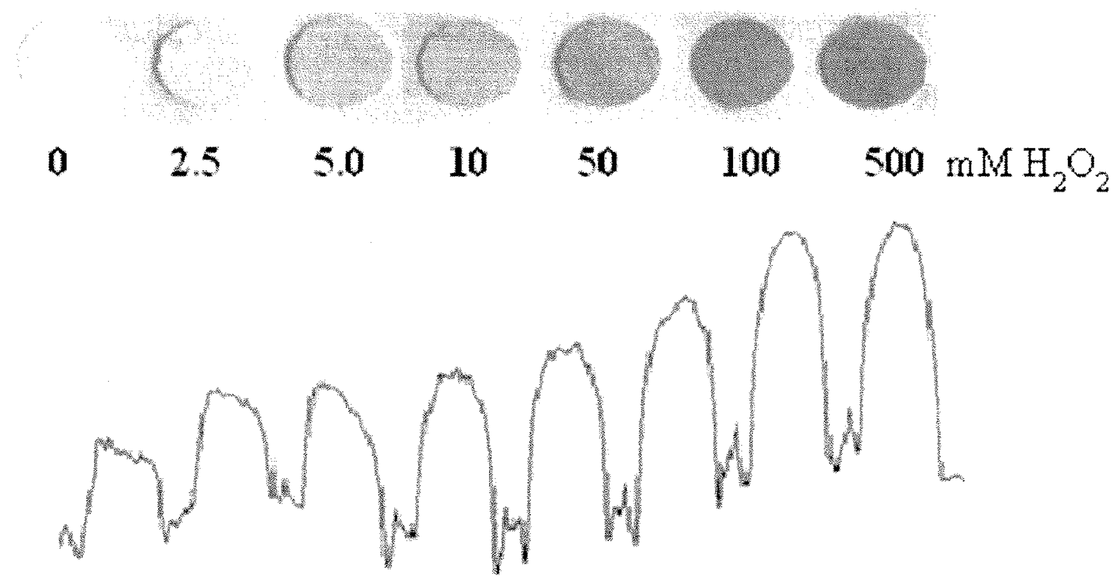
FIG. 2B is a ceria-based colorimetric device on a paper substrate for semi-quantitative analysis of hydrogen peroxide, with the intensity of the color quantified using the ImageJ software.

An example of test device in the present invention, in a very simple form is shown in FIGS. 2 and 4 where Whatman filter paper was used as supporting material for the colorimetric ceria-based composition. The paper support is loaded with the color changing ceria nanoparticles (in FIG. 1 for detection of hydrogen peroxide) and ceria nanoparticles and enzyme respectively (glucose oxidase (GOX) in FIGS. 3 and 4 for detection of glucose, as an example). The enzymatic test sensor was used for detection of glucose in a concentration range from 0.5-500 mM. The ceria and the enzyme can be deposited in a composite form using a polymeric or a silica-gel linker, and can contain stabilizing agents, additives; it can also be covered with stabilizing layers of polymers, hydrogels, porous silica-gels, etc.

This invention is not limited to any one application (i.e. color forming in the presence of hydrogen peroxide, antioxidants, or hydrogen peroxide formed in an enzymatic reaction, and color inhibiting reagents). In general, any system that reacts with ceria and determines its color change as a result of a redox process, or any system that generates hydrogen peroxide and gives a color change proportional to the quantity of the analyte can be employed.

In another aspect, this invention includes operation in anaerobic conditions of these systems (e.g. sensors based on oxidase enzyme). In the present invention, ceria nanoparticles act as an oxygen reservoir or oxygen storage/delivery vehicle. Oxidase enzymes use molecular oxygen as a co-substrate. In the absence of oxygen, these enzymes are not able to catalyze the oxidation of their specific substrates. The use of cerium oxide nanoparticles, in the intimate contact or proximity of oxidase enzymes provides the oxygen needed to carry out the oxidation reaction, even in anaerobic conditions as shown in FIG. 5. The oxygen present on the ceria surface initiates the enzymatic reaction generating hydrogen peroxide. The formed hydrogen peroxide reacts with ceria, changing the oxidation state and releasing oxygen in the process, thus providing the oxygen necessary for the enzymatic reaction:

$$2CeO_2+H_2O_2 \rightarrow Ce_2O_3+O_2+H_2O$$

$$CeO_2+H_2O_2 \rightarrow Ce(OH)_2+O_2$$

$$CeO_2+2H_2O_2 \rightarrow Ce(OH)_4+O_2$$

The aspect described above is not limited to any one enzyme. In general, any enzyme that requires oxygen as a co-substrate can be employed. Further, the aspect described above refers to nanoparticles of: ceria, ceria doped and binary and tertiary mixture of ceria with other metal oxides. Doped forms and mixtures of ceria based materials have higher oxygen storage capacity due to defective structures. Ceria doped particles refers to ceria doped with any, or a combination of the following elements: platinum, gold, palladium, manganese, osmium, gadolinium, samarium, niobium, dysprosium, erbium, germanium, holmium, indium, iridium, molybdenum, neodymium, rhodium, tantalum, tungsten, yttrium, zirconium, ytterbium, thulium, terbium, and praseodymium. Mixtures of ceria based metal oxides and ceria based composites include binary or tertiary mixtures of ceria with any of the following components and alike: titania, yttria, zirconia, gadolinia, samaria, niobia, etc.

The aspects described above apply to any system in which oxygen is required for biocatalysis and bioanalysis in conditions of oxygen depletion. Two such examples are listed here but the invention is not limited to those: implantable devices with immobilized biocatalysts designed for in vivo uses where there is a limited oxygen concentration, anaerobic fermentors for quantification of fermentation parameters. For such applications, the materials described herein can be used in solution or immobilized onto solid supports. Both optical and electrochemical detection systems can be used. Examples of solid supports are: paper, electrodes, glass, etc.

The devices described in the present invention can be disposable (used for one analysis), or can be used multiple times after regeneration (several hours after use the devices regenerates by itself by decomposing the hydrogen peroxide; slight heating can be used to increase the decomposition rate).

The methods and devices described herein can also comprise the direct detection of antioxidant without the presence of hydrogen peroxide. Antioxidants can include any antioxidant that creates a color change in the sensor, including but not limited to ascorbic acid, gallic acid, vanillic acid, caffeic acid, trolox, resveratrol, and/or quercetin, for example. For example, a series of experiments were conducted using ascorbic acid to study the interaction of ceria with an antioxidant. It was observed that when ascorbic acid was added to 4% ceria, APTS papers, a pink color ensued. It was of interest to determine whether this color was concentration dependant, so 15, 10, 5, 4, 3, 2, and 1 mM ascorbic acid were added to a series of papers and three trials for each concentration were done. The addition of antioxidant to the ceria sensors resulted in a color change, with the strongest response seen at 1 mM and greater.

In another series of experiments, when ascorbic acid was added to 4% ceria sensors, which were yellow from hydrogen peroxide addition, the color decreased until all ceria-peroxide complexes were broken. It was observed that when a high concentration of $H_2O_2$ was used, such as 100 mM, the color was merely reduced, rather than changed to pink, within the same range of concentrations used above. In fact, this method appeared to be much more sensitive, since a significantly large color reduction was seen even with addition of 10 nM ascorbic acid to 100 mM H2O2 containing 4% ceria papers. In contrast, 25 uM of ascorbic acid on the 4% ceria papers alone showed little color production.

Applications

There are many applications of this invention. The disclosed device is particularly suitable for on-site detection in any applications involving uses of hydrogen peroxide, antioxidants as well as for point-of-care diagnosis. Two main areas are identified where detection of hydrogen peroxide is important: (1) cleaning/water monitoring where concentrations of hydrogen peroxide are significant and (2) physiological/biomedical applications, where hydrogen peroxide is present in lower concentrations and often as a secondary product of enzymatic reactions. Sensor patches for monitoring the quality of food products are also possible. Ceria based sensor strips for the detection of the antioxidant content (for example food antioxidants) to determine the antioxidant capacity are also covered by this invention. Examples of applications are provided below to illustrate the invention, but these are not construed as limiting the scope of the invention. The particular materials, analytes, type of sample, amounts thereof, products, physical testing equipment in these examples, as well as other conditions and details, are to be interpreted to apply broadly in the art and should not be construed to unduly restrict or limit the invention in any way.

Materials Used

Potential materials to be used in one or more of the following examples are: (1) ceria nanoparticles—colloidal solution with particles having a diameter ranging from 2-20 nm (non-agglomerated, smaller size particles are preferred as they will provide higher surface area and higher intensity of the color and therefore lower detection limit and higher sensitivity), hydrogen peroxide, antioxidants such as ascorbic acid, gallic acid, vanillic acid, caffeic acid, trolox, resveratrol, quercetin, etc Watman filter paper, glass test tube, chitosan, alginic acid, calcium chloride ($CaCl_2$), carboxymethylcellulose (CMC), aminopropyltriethoxysilane (APTS), tetraethylsilane (TES), tetraethyl orthosilicate (TEOS), tetramethyl orthosilicate (TMOS), sodium tripolyphosphate (NaTPP), glucose, glucose oxidase, lactate, lactate oxidase, glutamate, glutamate oxidase, xanthine, xanthine oxidase, billirubin, billirubin oxidase, ethanol, alcohol oxidase, lactose, galactose, galactosidase. The optimum amounts of active components (e.g. nanoparticles, enzymes, additives) can be varied to tailor the desired performance of the device in the useful concentration range according to a particular sample or application. A suitable, optimal configuration can be determined experimentally.

Example of Preparation of a Ceria Based Substrate.

Used here to illustrate the concept is commercial Watman filter paper. To create ceria-modified paper as a sensing surface: defined sensing spots of Whatman filter paper are immersed for 10 minutes in 3% cerium oxide aqueous colloidal nanoparticle solution and then dried at 100° C. The so-prepared ceria-modified sensing paper is immersed in 5% APTS in ethanol for 10 minutes and then dried at 100° C. for 10 additional minutes. The ceria based paper is used for measuring hydrogen peroxide containing samples. Alteration of the amount of ceria or size of nanoparticles can be used to tailor the sensitivity of the sensing area to the useful concentration range, according to specific sample and application and can be determined through experimentation.

Enzyme-modified ceria paper: fresh ceria paper prepared as described above is soaked in 1% chitosan, prepared in 0.5% succinic acid solution for 10 minutes, and air dried for 5-10 minutes. The following treatment is used to immobilize the enzyme: (1) the paper is immersed in 5% glutaraldehyde for 1 minute, (2) air dried for 5-10 minutes, (3) enzyme (e.g. 9 mg/mL glucose oxidase) is added directly to each test spot and allowed to react for 5 minutes, (4) rinsed with water and (5) air dried.

A Ceria-paper Based Colorimetric Test Device for Determining Hydrogen Peroxide.

A defined spot of ceria-modified support is exposed to or dipped in a sample containing hydrogen peroxide (e.g. cleaning or disinfecting compositions). Upon contact, ceria is immediately changing the color to reddish-orange depending on the amount of hydrogen peroxide present in that composition (FIG. 2). The color change is compared visually with that of standard ceria-based paper spots obtained with known amounts of hydrogen peroxide or quantified using imaging software (ImageJ, Adobe, etc) as shown in FIG. 2.

A Ceria-paper Based Colorimetric Test Device for Determining Antioxidant Content.

A defined spot of ceria-modified support is exposed to or dipped in a sample containing antioxidants (e.g. tea, food extracts). Upon contact, ceria is immediately changing the color to dark brown or pink-red, depending on the type of sample and concentration of antioxidants. The color change is compared visually with that of standard ceria-based paper spots obtained with known amounts of antioxidants and quantified using imaging software (ImageJ, Adobe, etc).

A Test Device for Determining Ethanol Concentrations in Fluids and Human Breath.

A device comprising of ceria nanoparticles and alcohol oxidase in solution, co-immobilized or fixed onto a test tube (e.g. glass, plastic, etc) might be used to detect the presence of breath ethanol of an alcohol-user by blowing air into the test tube. Determination in saliva or whole serum by application of a drop of sample onto a ceria-alcohol oxidase modified surface (e.g. ceria-based paper as described above or a cotton swab) is also possible. When present in the sample, ethanol diffuses thorough the ceria-enzyme composite layer where the alcohol oxidase catalyzes the conversion of ethanol to hydrogen peroxide. The hydrogen peroxide that is formed will interact with the ceria nanoparticles, changing the color. The color change and the intensity of the color is an indication of the level of ethanol present.

A Device for Estimating Ethanol Production in Anaerobic Fermentation Processes.

A test device as the one described above is used in a fermentation reactor or anaerobic bioreactor to determine the amount of ethanol produced in the fermentation process.

A Colorimetric Ceria Based Biosensor for Determining Glucose.

Glucose oxidase-modified ceria supports are dipped in samples containing glucose. Color develops within several minutes. The change is visible with the naked eye (FIG. 4). The amount of glucose is estimated by comparing the color formed with that obtained with standard solutions of glucose. The enzymatic biosensor is used to detect glucose in the 0.5-500 mM concentration range with naked eye. For more precise quantification, the supports can be photographed or scanned with a flat-bed office scanner. Images are analyzed using imaging software (ImageJ, Adobe, etc) and compared. This biosensor is for use in clinical or home settings. For example, the device is suitable for analyzing glucose in body fluids (whole blood, saliva) and in food products (e.g. juice, tea, etc). The assay shows sensitivity for detection of physiological glucose concentrations, it is robust, inexpensive and performs successfully in human serum samples. One application for the detection of physiological levels of glucose in human serum sample is illustrated in FIG. 6.

A Colorimetric Ceria Based Biosensor for Determining Cholesterol.

Another example is a specific ceria based colorimetric biosensor for cholesterol detection. Here, cholesterol-oxidase is immobilized in close contact with ceria. When cholesterol is present, cholesterol-oxidase will convert cholesterol to hydrogen peroxide that will then be detected by the color change of ceria.

A Colorimetric Ceria Based Biosensor for Determining Lactate.

In another example of a specific ceria based device is a biosensor with lactate oxidase immobilized on a basic ceria-modified sensor, producing hydrogen peroxide in the presence of lactate in solution. The hydrogen peroxide will then be detected by the ceria-based colorimetric component. The same principle can be applied to glutamate using glutamate oxidase. Both clinical (e.g. cerebrospinal fluid) and food samples (e.g. the level of glutamate, used as additive in food) can be analyzed.

A Ceria Based Patch for Food Packaging to Estimate Changes in the Redox Status Related to Food Freshness.

A ceria based sensor patch is attached to the interior of food packaging to determine the release of free radicals or release of hydrogen peroxide. The patch contains ceria when used to estimate the peroxide content. In a modified version, the device contains xanthine oxidase when used to determine the production of free radicals. The patch is conveniently located in the food package in a clear transparent window. If food is degraded, the color of the patch changes to yellow-reddish depending on the extent of degradation and the amount of peroxide or superoxide radicals released. This patch is for use in food packages in stores, deposits or at home. The device is suitable for monitoring the freshness of packaged food that releases hydrogen peroxide or free radicals, when degraded. In addition, ceria by itself has antioxidant activity and thus a device based on this principle can provide, in addition to detection, removal capacity of the antioxidant formed. The invention includes the use of such patches (or other supports) for both detection and antioxidant action (inactivation of free radicals) purposes.

A Test Device for Determining the Amount of Enzyme Inhibitors in a Sample.

This application is an example of analysis of chemicals that inhibit the desired chemical or enzymatic reaction in the test strip by preventing the formation of the color. Exemplified here is the determination of antioxidant substances which inactivate free radicals formed in an enzymatic reaction between xanthine (or hypoxanthine) and xanthine oxidase. Superoxide radicals generated in the presence of xanthine oxidase change the color of the colorimetric ceria based component. In the presence of antioxidants, the antioxidants will inactivate the free radicals as they are formed, preventing the color change, to an extent proportional to their relative concentration.

A Ceria Based Oxidase Enzyme Component Used in Anaerobic Conditions.

A composite comprising of ceria is used to provide oxygen in anaerobic environments (FIG. 5).

A Ceria Based Composite Material for Biofuel Cells.

A ceria based composite is used to provide oxygen in biofuel cells. A homogenous composite comprising of ceria or doped ceria, oxidase enzymes such as laccase, glucose oxidase, etc. in conjunction or not with conductive materials, is used as anode or cathode coating material in biofuel cells.

A Ceria Based Composite Material for Implantable Biosensors (e.g. Implantable Glucose, Glutamate, Lactate Sensors).

A ceria based composite is used to provide oxygen in an implantable sensor based on the use of oxidase enzymes (e.g. glucose oxidase, lactate oxidase, glutamate oxidase). A homogenous composite comprising of ceria (or doped or mixed ceria based oxides), and an oxidase enzyme such as glucose oxidase in conjunction or not with conductive materials such as carbon or conductive polymers (e.g. polyaniline), is used as electrode coating of an implantable device to be used in vivo.

Ceria Based Contact Lenses for the Detection of Glucose in Tears.

A ceria based composite with glucose oxidase enzyme is used to coat the surface of contact lenses to determine glucose concentrations in tears. This is a type of wearable, non-invasive biosensor that can be used by individuals with diabetes. All components are biocompatible and the ceria nanoparticles have antioxidant properties: thus it could also serve a therapeutic function in the healing of eye wounds, be reducing levels of reactive oxygen species, further preventing scarring and damage to the area.

The foregoing is provided for the purpose of illustrating, explaining and describing embodiments of the present invention. Further modifications and adaptations to these embodiments will be apparent to those skilled in the art and may be made without departing from the spirit of the invention or the scope of the following claims.

What is claimed is:

1. A method for the colorimetric detection of hydrogen peroxide in a sample, the method comprising the steps of:

providing a colorimetric reagent comprising a plurality of ceria nanoparticles;

contacting the colorimetric reagent with the sample to form a mixture; and measuring an optical property of the mixture, wherein a change in the optical property of the mixture is associated with the presence of hydrogen peroxide in the mixture.

2. The method of claim 1, wherein the colorimetric reagent is immobilized to a support.

3. The method of claim 1, further comprising the step of:

comparing the optical property of the mixture to a predetermined value.

4. The method of claim 1, wherein the plurality of ceria nanoparticles comprise cerium oxides in at least two different valence states.

5. The method of claim 1, further comprising the step of:

reusing the colorimetric reagent.

6. The method of claim 1, wherein said ceria nanoparticles are doped with a metal.

7. The method of claim 1, wherein the change in the optical property of the mixture varies depending upon the size and concentration of the plurality of ceria nanoparticles.

8. A method for the colorimetric detection of an analyte in a sample, the method comprising the steps of:

providing a colorimetric reagent comprising a plurality of ceria nanoparticles and a plurality of analyte-specific oxidase enzyme molecules;

contacting the colorimetric reagent with a sample to form a mixture, wherein at least some of the plurality of analyte-specific oxidase enzyme molecules react with the analyte to form hydrogen peroxide; and measuring an optical property of the mixture, wherein a change in the optical property of the mixture is associated with the presence of hydrogen peroxide in the mixture.

9. The method of claim 8, wherein the change in the optical property is proportional to the concentration of the analyte in the sample.

10. The method of claim 8, wherein the colorimetric reagent is immobilized to a support.

11. The method of claim 8, wherein the colorimetric reagent does not comprise a dye.

12. The method of claim 8, further comprising the step of:

comparing the optical property of the mixture to a predetermined value.

13. The method of claim 8, wherein the plurality of ceria nanoparticles comprise cerium oxides in at least two different valence states.

14. The method of claim 8, further comprising the step of:

reusing the colorimetric reagent.

15. The method of claim 8, wherein the plurality of ceria nanoparticles have a diameter ranging from about 2 nm to about 20 nm.

16. The method of claim 8, wherein the step of contacting the colorimetric reagent with a sample to form a mixture comprises contacting the colorimetric reagent with a sample under anaerobic conditions.

17. The method of claim 9, wherein said ceria nanoparticles are doped with a metal.

18. The method of claim 6, wherein said metal is gold.

19. The method of claim 17, wherein said metal is gold.

* * * * *